Patent …

United States Patent [19]
Maurer et al.

[11] Patent Number: 4,882,321
[45] Date of Patent: Nov. 21, 1989

[54] THIONOPHOSPHONIC ACID ESTER ARTHROPODICIDES

[75] Inventors: Fritz Maurer, Wuppertal; Herbert Sommer, Remscheid; Wolfgang Behrenz, Overath; Bernhard Homeyer, Leverkusen; Wilhelm Stendel, Wuppertal, all of Fed. Rep. of Germany

[73] Assignee: Bayer Aktiengesellschaft, Leverkusen, Fed. Rep. of Germany

[21] Appl. No.: 152,521

[22] Filed: Feb. 5, 1988

[30] Foreign Application Priority Data

Feb. 14, 1987 [DE] Fed. Rep. of Germany ....... 3704689

[51] Int. Cl.$^4$ .......................... A01N 57/24; C07F 9/65
[52] U.S. Cl. ......................................... 514/86; 544/243
[58] Field of Search .......................... 544/243; 514/86

[56] References Cited

U.S. PATENT DOCUMENTS

| | | | |
|---|---|---|---|
| 4,115,542 | 9/1978 | Maurer et al. | 514/86 |
| 4,150,159 | 4/1979 | Maurer et al. | 514/86 |
| 4,152,426 | 5/1979 | Maurer et al. | 514/86 |
| 4,188,383 | 2/1980 | Maurer et al. | 514/86 |

FOREIGN PATENT DOCUMENTS 2351989 12/1977 France.
2365578  4/1978 France.

*Primary Examiner*—Mukund J. Shah
*Assistant Examiner*—Diana G. Rivers
*Attorney, Agent, or Firm*—Sprung, Horn, Kramer & Woods

[57] ABSTRACT

Arthropodicidally active O-(6-alkoxy-2-tert-butyl-pyrimidin-4-yl)-O-methyl-thionoethanephosphonic acid diesters of the formula

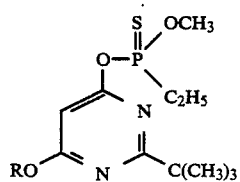

in which R represents alkyl with 1 to 4 carbon atoms or cycloalkyl with 3 or 4 carbon atoms. The intermediate where R is replaced by H is also new.

8 Claims, No Drawings

THIONOPHOSPHONIC ACID ESTER ARTHROPODICIDES

The invention relates to new O-(6-alkoxy-2-tert-butyl-pyrimidin-4-yl)-O-methyl-thionoethanephosphonic acid diesters, to processes and to a new intermediate product for their preparation and also to their use as pest combating agents, preferably as insecticides.

It is already known that certain O-(6-alkoxy-2-alkyl-pyrimidin-4-yl)-O-alkyl-thionoalkanephosphonic acid diesters, such as, for example, O-(6-ethoxy-2-iso-propyl-pyrimidin-4-yl)-O-methyl-thionoethanephosphonic acid diester, O-(6-methoxy-2-isopropyl-pyrimidin-4-yl)-O-methylthionoethanephosphonic acid diester, O-(6-ethoxy-2-ethyl-pyrimidin-4-yl)-O-methyl-thionoethanephosphonic acid diester and O-(6-methoxy-2-iso-propyl-pyrimidin-4-yl)-O-methyl-thionomethanephosphonic acid diester, are suitable for combating insects (compare DE-OS (German Published Specification) No. 2,642,981 corresponding to U.S. Pat. No. 4,150,159. The insecticidal action of these known compounds is not always satisfactory, however, especially at lower application rates or active compound concentrations and in respect of the duration of action.

New O-(6-alkoxy-2-tert-butyl-pyrimidin-4-yl)-O-methyl-thionoethanephosphonic acid diester of the general formula (I)

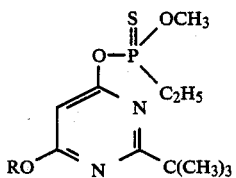

in which R represents alkyl with 1 to 4 carbon atoms or cycloalkyl with 3 or 4 carbon atoms, have now been discovered.

It has also been discovered that the new O-(6-alkoxy-2-tert-butyl-pyrimidin-4-yl)-O-methyl-thionoethanephosphonic acid diesters of the formula (I) are obtained when (a) 6-alkoxy-2-tert-butyl-4-hydroxy-pyrimidines of the general formula (II)

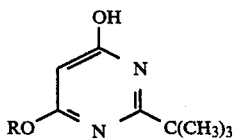

in which R has the meaning given above, are reacted with thionoethanephosphonyl chloride methyl ester of the formula (III)

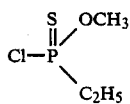

if appropriate in the presence of an acid acceptor and if appropriate in the presence of a diluent, or (b) O-(6-hydroxy-2-tert-butyl-pyrimidin-4-yl)-O-methylthionoethanephosphonic acid diester of the formula (IV)

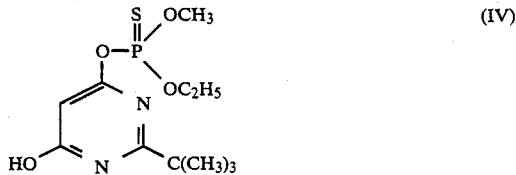

is reacted with alkylating agents of the general formula (V)

R—X    (V)

in which
R has the meaning given above and
X represents a nucleofugic leaving group,
if appropriate in the presence of an acid acceptor and if appropriate in the presence of a diluent.

Finally, it has been discovered that the new O-(6-alkoxy-2-tert-butyl-pyrimidin-4-yl)-O-methyl-thionoethanephosphonic acid diesters of the formula (I) are characterized by very strong arthropodicidal, in particular insecticidal, activity.

The new compounds of the formula (I) show, in particular, an outstanding, long-lasting action against Diptera, such as, for example, *Musca domestica*, on basic substrates, and also such as, for example, on limed walls, and also on wood or plywood. The active compounds according to the invention also exhibit outstanding action against soil insects (that is, insects which occur in or on the soil or in its vicinity), such as, for example, *Phorbia antiqua* grubs and *Diabrotica balteata* larvae.

Surprisingly, the O-(6-alkoxy-2-tert-butyl-pyrimidin-4-yl)-O-methyl-thionoethanephosphonic acid diesters of the formula (I), according to the invention, show considerably better and/or longer-lasting insecticidal action than the abovementioned O-(6-alkoxy-2-alkyl-pyrimidin-4-yl)-O-alkyl-thionoalkanephosphonic acid diesters. The substances according to the invention therefore represent a valuable enrichment of the art.

In the general formulae (I), (II) and (V), alkyl and cycloalkyl represent methyl, ethyl, n-propyl, n-butyl, isopropyl, isobutyl, sec-butyl, tert-butyl, cyclopropyl or cyclobutyl, preferably methyl, ethyl, n-propyl, isopropyl or cyclopropyl, particularly methyl or ethyl.

The invention thus preferably relates to compounds of the formula (I) in which R represents methyl, ethyl, n-propyl, isopropyl or cyclopropyl, in particular compounds of the formula (I) in which R represents methyl or ethyl.

Particularly important compounds of the formula (I) which may be mentioned are: O-(6-methoxy-2-tert-butyl-pyrimidin-4-yl)-O-methyl-thionoethanephosphonic acid diester and O-(6-ethoxy-2-tert-butyl-pyrimidin-4-yl)-O-methyl-thionoethanephosphonic acid diester.

If, for example, 6-methoxy-2-tert-butyl-4-hydroxypyrimidine and thionoethanephosphonyl chloride methyl ester are used as starting substances in the process variant (a), then the course of the reaction can be represented by the following scheme:

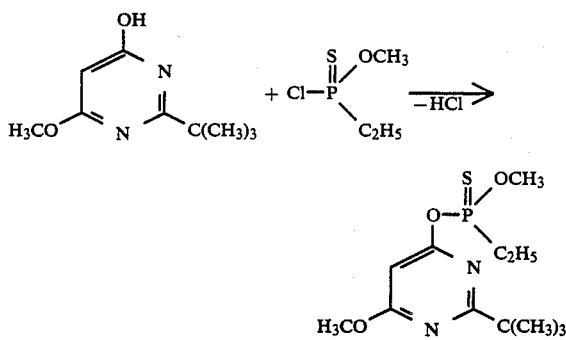

If, for example, O-(6-hydroxy-2-tert-butyl-pyrimidin-4-yl)-O-methyl-thionoethanephosphonic acid diester and ethyl bromide are used as starting substances in the process variant (b), then the course of the reaction can be represented by the following scheme:

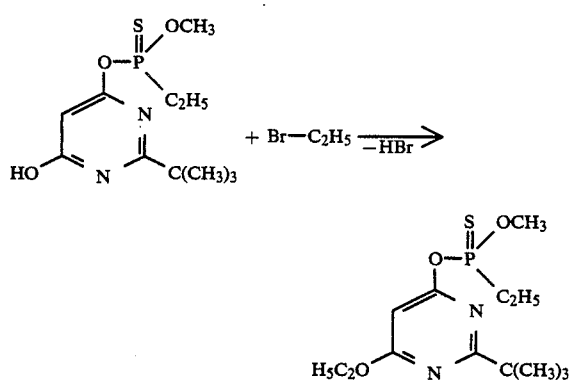

A general definition of the 6-alkoxy-2-tert-butyl-4-hydroxy-pyrimidines to be employed as starting substances in process variant (a) is given by the formula (II). Starting substances of the formula (II) in which R represents methyl, ethyl, n-propyl, isopropyl or cyclopropyl are preferred.

Starting substances of the formula (II) in which R represents methyl or ethyl are particularly preferred. 6-Methoxy-2-tert-butyl-4-hydroxy-pyrimidine and 6-ethoxy-2-tert-butyl-4-hydroxy-pyrimidine may be mentioned as examples.

The 6-alkoxy-2-tert-butyl-4-hydroxy-pyrimidines of the formula (II) are known (compare DE-OS (German Published Specification) 2,642,981).

The compounds of the formula (II) are obtained in a particularly advantageous manner when pivalamidine or an acid adduct thereof, such as, for example, pivalamidine hydrochloride, is reacted with a dialkyl malonate, such as, for example, diethyl malonate, in the presence of a strong base, such as, for example, sodium methylate, and in the presence of a diluent, such as, for example, methanol, at temperatures between 10° C. and 80° C., the mixture is evaporated after stirring for several hours, and the residue is taken up in water and adjusted with hydrochloric acid to a pH value between 7 and 10 and then an alkylating agent, such as, for example, dimethyl sulphate or diethyl sulphate, and sodium hydroxide solution are simultaneously metered in so that the pH value is kept in the range given above. The product of the formula (II) which is precipitated in crystalline form after the end of the reaction and, if appropriate, after cooling with ice is isolated by filtering off with suction.

The thionomethanephosphonyl chloride methyl ester of the formula (III) furthermore to be used as a starting substance in the process variant (a) is already known (compare DE-AS (German Published Specification) No. 1,078,124, British Patent Specification No. 1,450,284 and DE-OS (German Published Specification) No. 2,920,172).

The O-(6-hydroxy-2-tert-butyl-pyrimidin- 4-yl)-O-methyl-thionoethanephosphonic acid diester of the formula (IV) to be used as a starting substance in the process variant (b) is not yet known in the literature and is part of the present invention.

The new O-(6-hydroxy-2-tert-butyl-pyrimidin-4-yl)-4-yl)-O-methyl-thionoethanephosphonic acid diester of the formula (IV) is obtained when 4,6-dihydroxy-2-tert-butyl-pyrimidine of the formula (VI)

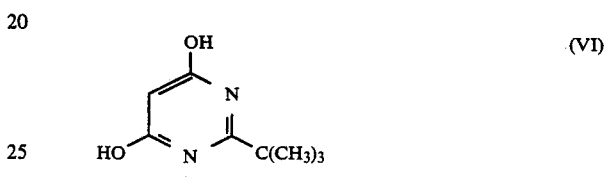

is reacted with thionoethanephosphonyl chloride methyl ester of the formula (III)

in the presence of an acid-binding agent, such as, for example, potassium carbonate or triethylamine, and in the presence of a diluent, such as, for example, acetonitrile or methylene chloride, at temperatures between −20° C. and +80° C., preferably between 0° C. and 50° C. For working up, the reaction mixture, if appropriate after evaporation, is shaken with water and with a practically water-immiscible organic solvent, such as, for example, toluene or methylene chloride, and the organic phase is separated off and evaporated under reduced pressure, whereupon the product of the formula (IV) remains as a residue.

The starting substance of the formula (VI) is already known (compare J. Heterocycl. Chem. 13 (1976), 1141–1144), likewise the starting substance of the formula (III)—see above.

A general definition of the alkylating agents furthermore to be used as starting substances in the process variant (b) is given by the formula (V).

Those starting substances of the formula (V) are preferred in which R represents methyl, ethyl, n-propyl, isoproppyl or cyclopropyl and the nucleofugic leaving group X represents halogen, especially chlorine, bromine or iodine. Those starting substances of the formula (V) are particularly preferred in which R represents methyl or ethyl and X represents chlorine, bromine or iodine. Methyl chloride, methyl bromide and methyl iodide and also dimethyl sulphate, ethyl chloride, ethyl bromide and ethyl iodide and also diethyl sulphate, and in addition isopropyl bromide and cyclopropyl chloride, may be mentioned as examples.

The alkylating agents of the formula (V) are known synthetic chemicals.

The process variants (a) and (b) according to the invention for the preparation of the new compounds of the formula (I) are preferably carried out with the use of diluents and acid acceptors.

Practically all inert organic solvents are suitable as diluents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethyl such as, for example, dimethylformamide, dimethylacetamide and N-methylpyrrolidone and also dimethylsulphoxide, tetramethylene sulphone and hexamethylphosphoric triamide.

In the process variants (a) and (b) according to the invention, all acid-binding agents usually utilizable for reactions of this type can be employed as acid acceptors. Those which are preferably suitable are alkali metal hydroxides such as, for example, sodium hydroxide and potassium hydroxide, alkaline earth metal hydroxides, such as, for example, calcium hydroxide, alkali metal carbonates and alkali metal alcoholates, such as sodium carbonate and potassium carbonate, sodium tert-butylate and potassium tert-butylate, and also aliphatic, aromatic or heterocyclic amines, for example triethylamine, trimethylamine, dimethylaniline, dimethylbenzylamine, pyridine, 1,5-diazabicyclo[4,3,0]-non-5-ene (DBN), 1,8-diazabicyclo-[5,4,0]-undec-7- ene (DBU) and 1,4-diazabicyclo-[2,2,2]-octane (DABCO).

In the process variants (a) and (b) according to the invention, the reaction temperatures can be varied within a relatively large range. In general, temperatures between 0° C. and 100° C., preferably between 10° C. and 80° C., are used.

The process variants (a) and (b) according to the invention are in general carried out at atmospheric pressure. It is also possible, however, to work at increased or reduced pressure.

In carrying out the process variant (a) according to the invention, the starting substances of the formulae (II) and (III) are generally employed in approximately equimolar amounts. An excess of one component or the other of up to about 10% is, however, possible without any problems.

The reaction components are generally added together in one of the solvents given above and and stirred for several hours, with the temperature being kept within the range given above.

For working up according to customary methods, the mixture is evaporated and the residue is taken up in a practically water-immiscible solvent, such as, for example, toluene, washed with water and dried with a customary drying agent, such as, for example, sodium sulphate. After filtration the solvent is distilled off from the filtrate under water pump vacuum.

The new compounds deposit in the form of oils, which can only partially be distilled without decomposition, but which by so-called "incipient distillation", i.e. by relatively long heating under reduced pressure at moderately raised temperatures, are freed from the final volatile constituents and purified in this manner. The refractive index may be used for their characterization.

For carrying out the process variant (b) according to the invention, between 1 and 3 mols preferably between 1.1 and 1.5 mols of the alkylating agent of the formula (V) are generally employed per mol of the compound of the formula (IV).

The reaction components are generally added together in one of the solvents given above and stirred for several hours, with the temperature being kept in the range given above. The work-up may be as given above for the process variant (a).

The active compounds are suitable for combating arthropods, in particular insects, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and *Scutigera spec. From the order of the Symphyla, for example, Scutigerella immaculata* From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Felt:a spp., *Earias insulana,* Heliothis spp., *Spodoptera exigua, Mamestra brassicae, Panolis flammea, Prodenia litura,* Spodoptera spp., *Trichoplusiani, Caprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Atlagenus spp., Lyctus spp., *Meligethes aeneus,* Ptinus spp., *Niptus hololeucus, Gibbium psylloides,* Tribolium spp., Tenebrio molitor, Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus. Oscinella frit,* Phorbia spp., *Pegomyia hyoscyami, Ceratitis capitata, Dacus oleae* and *Tipula paludosa.*

Some of the active compounds according to the invention also exhibit acaricidal action.

The active compounds according to the invention are characterized by outstanding insecticidal activity; particularly in the control of resistant Diptera, such as, for example,. *Musca domestica.* Their action is also very long-lasting on basic substrates, such as, for example, on limed walls and also on wood or plywood. The compound of the formula (I) in which R represents methyl is particularly preferred for these uses.

The active compounds according to the invention can also be used to very good effect for combating of soil insects, such as, for example, *Phorbia antiqua* grubs and *Diabrotica balteata* larvae, on account of their high stability. The compounds of the formula I in which R represents methyl or ethyl (particularly ethyl) are particularly preferred for these uses.

The compounds of the formula (I) according to the invention, particularly O-(6-methoxy-2-tert-butyl-pyrimidin-4-yl)-O-methyl-thionoethanephosphonic acid diester, are very particularly preferably used in the household and hygiene sector for combating Diptera, such as, for example, Musca domestica, which are resistant to many insecticides.

The active compounds of the formula (I) according to the invention are also suitable for combating arthropods, particularly insects, which infest agricultural productive livestock such as, for example, cattle, sheep, goats, horses, pigs, donkeys, camels, buffalo, rabbits, chickens, turkeys, ducks, geese and other pets, such as, for example, dogs, cats, cage birds, and also so-called test animals, such as, for example, hamsters, guinea pigs, rats and mice. By combating these insects, cases of death and reductions in productivity (for meat, milk, wool, hides, eggs etc,) should be diminished, so that more economic and simpler animal husbandry is possible by use of the active compounus according to the invention.

The active compounds according to the invention are used in the veterinary sector in a known manner by the application of suitable formulations, for example by sprays, dusts, coating the environment of the animals (for example stabled animals) or, where appropriate, also by dermal use in the form, for example, of dipping or bathing, spraying, pouring on and spotting on, washing and powdering, and also with the aid of molded articles containing the active compound, such as neckbands, ear marks, tail marks, limb bands, halters, marking devices, etc.

The active compounds can be converted to the customary formulations depending on their respective physical and/or chemical properties, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silicic acid, auumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

Preparation Examples

EXAMPLE 1

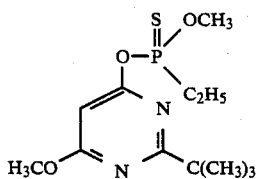

Process Variant (a)

16 g (0.096 mol) of thionoethanephosphonyl chloride methyl ester (95%) are added at 20° C. with stirring to a mixture of 17.9 g (0.098 mol) of 6-methoxy-2-tert-butyl-4-hydroxy-pyrimidine, 17.3 g (0.125 mol) of potassium carbonate and 200 ml of acetonitrile, and the mixture is stirred for about 15 hours at 20° C. After evaporation, the residue is taken up in 100 ml of toluene, and the solution is washed twice with 100 ml of water in each case, dried using sodium sulphate and filtered. The solvent is distilled off from the filtrate under reduced pressure at about 50° C.

27.8 g (95% of theory) of O-(6-methoxy-2-tert-butyl-pyrimidin-4-yl)-O-methyl-thionoethanephosphonic acid diester are obtained as an oily residue of refractive index $n_D^{22} = 1.5114$.

Process variant (b)

8.5 g (0.06 mol) of methyl iodide are added at 20° C. with stirring to a mixture of 14.5 g (0.05 mol) of O-(6-hydroxy-2-tert-butyl-pyrimidin-4-yl)-O-methyl-thionoethanephosphonic acid diester, 9 g (0.65 mol) of potassium carbonate and 80 ml of acetonitrile. The reaction mixture is stirred for 2 hours at 80° C. and evaporated under reduced pressure (in a water pump vacuum), and 150 ml of toluene are added. The residue is washed twice with 100 ml of water in each case, and dried over sodium sulphate. After filtration, the solvent is distilled off from the filtrate in a water pump vacuum and the residue is subjected to incipient distillation at 50° C.

13.7 g (90% of theory) of O-(6-methoxy-2-tert-butyl-pyrimidin-4-yl)-O-methyl-thionoethanephosphonic acid diester are thus obtained as an oily residue of refractive index $n_D^{20} = 1.5122$.

The compounds of the formula (I) listed in the following table can be prepared analogously to Example 1 and in correspondence with the general description of the processes of preparation according to the invention.

TABLE

Further examples of compounds of the formula (I)

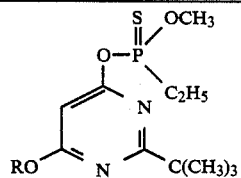

| Example No. | R | Refractive index |
|---|---|---|
| 2 | C$_2$H$_5$ | $n_D^{22}$ = 1.5096 |
| 3 | CH$_2$CH$_2$CH$_3$ | |
| 4 | CH(CH$_3$)$_2$ | |
| 5 | —CH(CH$_2$)(CH$_2$) | |

Starting substances of the formula (II)

EXAMPLE (II-1)

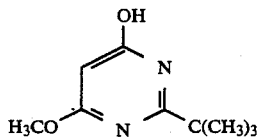

10.5 g of 26% solution of pivalamidine hydrochloride (0.02 mol) in methanol are mixed with 10.8 g of a 30% solution of sodium methylate (0.06 mol) in methanol and with 3.2 g (0.02 mol) of diethyl malonate. This mixture is heated to 60°C. with stirring for 2 hours, stirred for about 20 hours at 20°C. and evaporated. The residue is taken up in pb 10 ml of water, and the solution is adjusted to pH 8.2 using concentrated hydrochloric acid, and 6.5 g (0.04 mol) of dimethyl sulphate and concentrated sodium hydroxide solution are added dropwise at a rate such that the pH value remains between 8.0 and 8.5. The reaction mixture is then stirred for a further two hours at 50° C., the pH being maintained in the range given above by addition of sodium hydroxide solution. After cooling to 5° C. the product, which is precipitated in crystalline form, is isolated by filtering off with suction.

2.5 g (68% theory) of 6-methoxy-2-tert-butyl-4- hydroxy-pyrimidine of melting point 175° C. are obtained.
The following is obtained analogously:

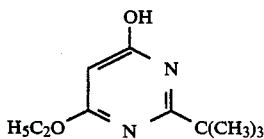

Melting point: 150–152° C.

Starting substance of the formula (IV)

EXAMPLE (IV-1)

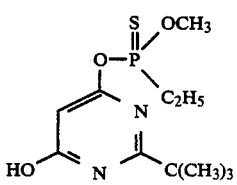

A mixture of 24.2 g (0.144 mol) of 4,6-dihydroxy-2-tert-butyl-pyrimidine, 15.2 g (0.15 mol) of triethylamine and 120 ml of methylene chloride is stirred for 30 minutes at 20° C. and then cooled to 5° C., and 19 g (0.12 mol) of thionoethanephosphonyl chloride methyl ester are added dropwise. The reaction mixture is stirred at 20° C. for 20 hours, washed twice with 50 ml of water in each case and evaporated in a water pump vacuum.

33.5 g (96% of theory) of O-(6-hydroxy-2-tert-butyl-pyrimidin-4-yl)-O-methyl-thionoethanephosphonic acid diester are thus obtained as a crystalline residue of melting point 119° C.

USE EXAMPLES

The compounds given below were employed as comparison compounds in some of the following use examples:

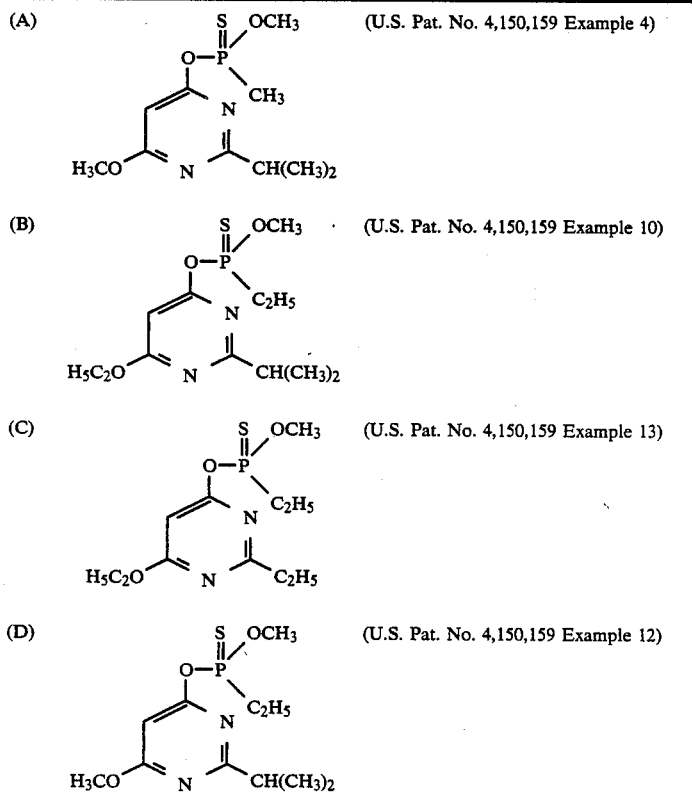

EXAMPLE A

Test insects: *Musca domestica* (resistant)
Number of test insects: 25
Solvent: acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filter paper of about 9.5 cm diameter is located on the bottom of the Petri dish. The Petri dish is left standing open until the solvent has completely evaporated. The amount of active compound per m² of filter paper varies, depending on the concentration of the active compound solution. The stated number of test insects is then introduced into the Petri dish, and the dish is covered with a glass lid.

The condition of the test insects is checked continuously. The time required for a 100% knock-down effect is determined.

In this test, the compound obtained according to Preparation Example (1) exhibited 100% action after 170 minutes at an active compound concentration of 0.002%, for example, whereas the comparison compounds (B), (C) and (D) only exhibited 70, 60 and 90% activity respectively after 360 minutes.

EXAMPLE B

Residual test
Test insects: Musca domestica (resistant)
Number of test insects: 25
Wettable powder base substance consisting of:
3% of sodium diisobutylnaphthalene-1-sulphonate
6% of sulphite waste liquor, partly condensed with aniline
40% of highly disperse silicic acid, containing CaO
51% of colloidal kaolin To produce a suitable preparation of active compound, 1 part by weight of active compound is intimately mixed with 9 parts by weight of wettable powder base substance. The sprayable powder thus obtained is suspended in 90 parts of water.

The suspension of active compound is sprayed in an application amount of, for example, 1 g of active compound per $m^3$ onto substrates of various materials.

The spray coatings are tested for their biological action at certain intervals of time.

For this purpose, the stated number of test insects is placed on the treated substrates. A shallow cylinder, the upper end of which is closed with a wire grid to prevent the insects from escaping, is placed over the test inseccs. The destruction of the test insects, in %, is determined within a residence time of the insects on the substrate of 8 hours. 100% means that all the test insects have been killed; 0% means that none of the test insects have been killed.

In this test, the compound obtained according to Preparation Example (1) exhibited 100% action on the test substrates (clay, clay limed with calcium hydroxide, plywood) even after 20 weeks in an application amount of 1 $g/m^2$, for example, whereas the comparison compound (A), even applied in twice the quantity, no longer shows any detectable action on the test substrates given above after 20 weeks.

EXAMPLE C

Critical concentration test/soil insects
Test insect: Phorbia antiqua grubs (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

The compounds obtained according to the Preparation Examples (1) and (2) exhibited 100% action in this test at an active compound concentration of 20 ppm, for example, whereas the comparison compound (A) showed no detectable action at this concentration. In addition, the compounds obtained according to the Preparation Examples (1) and (2) also showed 100% acion at an active compound concentration of 0.6 ppm, whereas the comparison compound (D) showed 50% action and the comparison compound (C) showed no detectable action.

EXAMPLE D

Critical concentration test/soil insects
Test insect: Diabrotica balteata larvae (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test insects are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

The compounds obtained according to the Prepararation Examples (1) and (2) exhibited 100% action in this test at an active compound concentration of 20 ppm, for example, whereas the comparison compound (A) showed no detectable action at this concentration. In addition, the compounds obtained according to the Preparation Examples (1) and (2) also showed 100% action at an active compound concentration of 0.6 ppm, whereas the comparison compound (C) showed 20% action and the comparison compound (D) showed no detectable action at this concentration.

EXAMPLE E

Test with *Lucilia cuprina* res. larvae (Goondi windi strain, OP-resistant)
Solvent:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* res. larvae are intorduced into a test tube which contains approx. 1 $cm^3$ of horse muscle and 0.5 ml of the preparation of active compound. After 24 hours, the degree of destruction is determined.

The compounds of Preparation Examples 1 and 2, for example, showed a degree of destruction of 100% at a concentration of 300 ppm, for example, in this test.

It will be appreciated that the instant specification and claims are set forth by way of illustration and not limitation, and that various modifications and changes may be made without departing from the spirit and scope of the present invention.

What is claimed is:

1. An O-(6-alkoxy-2-tert-butyl-pyrimidin-4-yl)-O-methylthionoethanephosphonic acid diester of the formula

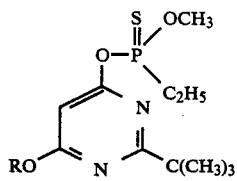

in which
R represents alkyl with 1 to 4 carbon atoms or cycloalkyl with 3 or 4 carbon atoms.

2. Compounds according to claim 1, in which R is alkyl with 1 to 4 carbon atoms.

3. A compound according to claim 1, wherein such compound is O-(6-methoxy-2-tert-butyl-pyrimidin-4-yl)-O-methyl-thionoethanephosphonic acid diester of the formula

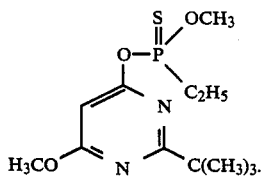

4. A compound according to claim 1, wherein such compound O-(6-ethoxy-2-tert-butyl-pyrimidin-4-yl)-O-methyl-thionoethanephosphonic acid diester of the formula

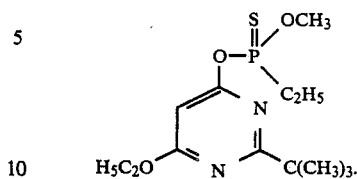

5. An arthropodicidal composition comprising an arthropodicidally effective amount of a compound according to claim 1 and a diluent.

6. A method of combating arthropods which comprises applying to such arthropods or to an arthropod habitat an arthropodicidally effective amount of a compound according to claim 1.

7. The method according to claim 6, wherein such compound is
O-(6-methoxy-2-tert-butyl-pyrimidin-4-yl)-O-methyl-thionoethanephosphonic acid diester, or
O-(6-ethoxy-2-tert-butyl-pyrimidin-4-yl)-O-methyl-thionoethanephosphonic acid diester.

8. The compound of the formula

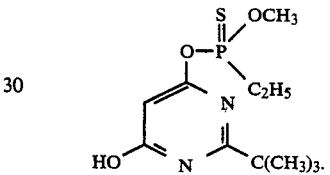

* * * * *